United States Patent [19]
Albert et al.

[11] Patent Number: 5,541,159
[45] Date of Patent: Jul. 30, 1996

[54] CALCITONIN DERIVATIVES

[75] Inventors: Rainer Albert, Basel; Wilfried Bauer, Lampenberg; François Cardinaux, Seewen; Janos Pless, Basel, all of Switzerland

[73] Assignee: Sandoz Ltd., Basel, Switzerland

[21] Appl. No.: 346,118

[22] Filed: Nov. 29, 1994

Related U.S. Application Data

[63] Continuation of Ser. No. 57,066, May 3, 1993, abandoned, which is a continuation of Ser. No. 916,284, Jul. 17, 1992, abandoned, which is a continuation of Ser. No. 781,789, Oct. 23, 1991, abandoned, which is a continuation of Ser. No. 334,969, Apr. 7, 1989, abandoned.

[30] Foreign Application Priority Data

Apr. 8, 1988 [GB] United Kingdom ............ 8808275
Apr. 12, 1988 [GB] United Kingdom ............ 8808528

[51] Int. Cl.⁶ ............ C07K 14/585; A61K 8/23
[52] U.S. Cl. ............ 514/8; 514/12; 514/15; 530/307; 530/322; 530/324; 530/328; 530/345
[58] Field of Search ............ 514/8, 12, 15; 530/307, 324, 328, 345, 322

[56] References Cited

U.S. PATENT DOCUMENTS 3,956,260  5/1976  Brugger et al. ............ 260/112.5 T
4,086,221  4/1978  Sakakibara et al. ............ 260/112.5 T

*Primary Examiner*—Howard E. Schain
*Attorney, Agent, or Firm*—Robert S. Honor; Melvyn M. Kassenoff; Thomas O. McGovern

[57] ABSTRACT

Peptide derivatives selected from (i) a calcitonin peptide and a LHRH antagonist peptide modified by at least one sugar residue and/or at least one short polyhydroxy compound or derivative, and (ii) a calcitonin peptide modified by at least one formyl and/or at least $C_{3-5}$alkyl attached to an amino group other than a N-terminal amino group, and (iii) a calcitonin peptide modified by a combination of said substituents, with the provisos that i) when the calcitonin peptide comprises at least one sugar residue a), this sugar residue is attached by a coupling other than a direct N-glycosidic bond to an ω-amino group of an ω-amino substituted side chain in the 24 position, and ii) when the LHRH antagonist comprises at least one sugar residue a), this sugar residue is an Amadori sugar residue attached by a coupling other than a direct N-glycosidic bond to an ω-amino group of an ω-amino substituted side chain in the 8 position in free form or in salt or complex form, have pharmacological activity.

4 Claims, No Drawings

CALCITONIN DERIVATIVES

This is a continuation of application Ser. No. 08/057,066, filed May 3, 1993, now abandoned, which in turn is a continuation of application Ser. No. 07/916,284, filed Jul. 17, 1992, which in turn is a continuation of application Ser. No. 07/781,789, filed Oct. 23, 1991, which in turn is a continuation of application Ser. No. 07/334,969, filed Apr. 7, 1989, the latter three of which are now abandoned.

The present invention relates to peptide derivatives having pharmaceutical activity, processes for their production, pharmaceutical preparations comprising them and their use as pharmaceuticals.

More particularly the present invention provides a peptide derivative selected from (i) a calcitonin peptide and a LHRH antagonist peptide and comprising attached to an amino group thereof at least a) one sugar residue or b) one residue of formula ($b_1$) or ($b_2$)

$$HOH_2C-(CHOH)_f-(C)_g-CH_2- \quad (b_1)$$
with $Y_1$ above and $Y_2$ below the central C $$HOH_2C-(CHOH)_f-CH-CH_2OH \quad (b_2)$$

wherein one of $Y_1$ and $Y_2$ is hydrogen and the other is hydroxy or both are hydrogen,
each of f and g independently is 0 or 1,
and the physiologically-acceptable ethers and physiologically-hydrolysable and -acceptable esters thereof or c) any combination from a) and b)
and (ii) a calcitonin peptide which comprises d) at least one formyl attached to an amino group other than a N-terminal amino group, or e) at least one $C_{3-5}$alkyl attached to an amino group other than a N-terminal amino group, or f) any combination from a), b), d) and e) above with the provisos that i) when the calcitonin peptide comprises at least one sugar residue a), this sugar residue is attached by a coupling other than a direct N-glycosidic bond to an ω-amino group of an ω-amino substituted side chain in the 24 position, and ii) when the LHRH antagonist comprises at least one sugar residue a), this sugar residue is an Amadori sugar residue attached by a coupling other than a direct N-glycosidic bond to an ω-amino group of an ω-amino substituted side chain the 8 position in free form or in salt or complex form.

Hereinafter, these compounds will be referred to as compounds of the invention.

In the compounds of the invention, the sugar residue a) may be attached to the amino group either directly by a linking other than a direct N-glycosidic bond or indirectly by a bridging member.

The term "sugar" is used therein to cover any mono- or oligosaccharide, especially a mono-, di- or triose or a derivative thereof, e.g. an amino- and/or carboxylic acid and/or reduced and/or esterified derivative thereof. The sugars may contain heptoses, hexoses and/or pentoses in their pyranoside or furanoside form.

In the following formulae, for the sake of simplicity, the sugar residue is usually only depicted by the structure of pyranoside or furanoside. Naturally e.g. open chain structures are also included in the invention.

Examples of sugar residues a) include for example

A) a residue of formula (Ia)

which is the deoxy residue of a ketose, the residue being linked via the $CH_2$ group to a NH group of the peptide as defined above,
preferably a residue of formula ($Ia_1$)

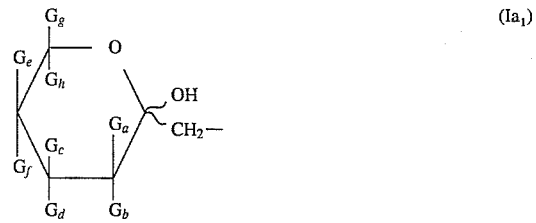

wherein
one of radicals $G_a$ and $G_b$ is hydrogen and the other is OH,
one of radicals $G_c$ and $G_d$ is hydrogen and the other is OH or O-glycosyl, wherein the glycosyl radical is derivable from a reducing mono-, di- or oligosaccharide,
one of radicals $G_e$ and $G_f$ is hydrogen and the other is OH,
one of radicals $G_g$ and $G_h$ is hydrogen and the other is hydrogen or $CH_2OH$,
e.g. wherein radicals $G_a$ to $G_h$ are selected such that the residue of formula ($Ia_1$) corresponds to a radical which is obtainable by means of an Amadori rearrangement from a natural or a synthetically accessible mono-, di- or oligosaccharide, for example deoxyfructosyl, deoxytagatosyl, deoxysorbosyl, α-glucosyl(1-4)-deoxyfructosyl, α-glucosyl(1-4)-α-glucosyl(1-4)-deoxyfructosyl,
or a residue of formula ($Ia_2$)

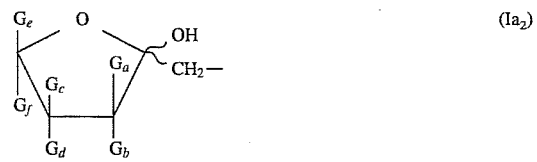

wherein
$G_a$, $G_b$, $G_c$ and $G_d$ are as defined above,
one of radicals $G_e$ and $G_f$ is hydrogen and the other is hydrogen, COOH, $CH_2OH$, $CH_2$-O-P(O)-(OH)$_2$ or $CH_2O$-glycosyl, wherein the glycosyl radical is derivable from a reducing mono-, di- or oligosaccharide,
e.g. wherein radicals $G_a$ to $G_f$ are selected such that the radical or formula ($Ia_2$) corresponds to a radical which is obtainable by means of an Amadori rearrangement from a natural or a synthetically accessible mono-, di- or oligosaccharide;

B) a residue of formula (Ib)

which is the deoxy residue of an aldose, the radical being linked via the free bond to a NH group of the peptide as defined above, preferably a residue of formula (Ib₁)

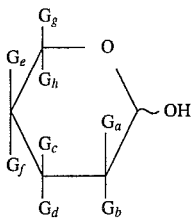
(Ib₁)

wherein
- one of radicals $G_a$ or $G_b$ is hydrogen and the other is a free bond,
- one of radicals $G_c$ or $G_d$ is hydrogen and the other is OH,
- one of radicals $G_e$ or $G_f$ is hydrogen and the other is OH or O-glycosyl, wherein the glycosyl radical is derivable from a reducing mono-, di- or oligosaccharide,
- one of radicals $G_g$ and $G_h$ is hydrogen and the other is $CH_2OH$, or $CH_2$-O-glycosyl, wherein the glycosyl radical is derivable from a reducing mono-, di- or oligosaccharide, e.g.
- wherein radicals $G_a$ to $G_h$ are selected such that the radical of formula (Ib₁) corresponds to a radical which is obtainable by means of a Heyns rearrangement from a natural or a synthetically accessible mono-, di- or oligoketose, for example D-fructose, lactulose, L-sorbose, D-tagatose or D-ribulose, or a residue of formula (Ib₂)

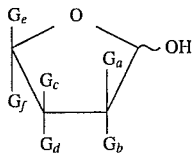
(Ib₂)

wherein
- $G_a$, $G_b$, $G_c$ and $G_d$ are as defined above,
- one of radicals $G_e$ and $G_f$ is hydrogen and the other is $CH_2OH$ or $CH_2$O-glycosyl, wherein the glycosyl radical is derivable from a reducing mono-, di- or oligosaccharide, e.g.
- wherein radicals $G_a$ to $G_f$ are selected such that the radical (Ib₂) corresponds to a radical which is obtainable by means of a Heyns rearrangement from a natural or a synthetically accessible mono-, di- or oligoketose, for example D-fructose, lactulose, L-sorbose, D-tagatose or D-ribulose;

C) a residue of formula (Ic)

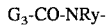
(Ic)

wherein
- $G_3CO$ is the residue of an uronic acid, e.g. glucuronic or galacturonic acid, or of a polyhydroxymono- or di-carboxylic acid, e.g. gluconic acid, glucaric acid, quinic acid, acetylmuramic acid, acetylneuraminic acid or D-glucosaminic acid, and
- Ry is hydrogen, $C_{1-3}$alkyl or $C_{1-4}$alkanoyl;

D) a residue of formula (Id₁) to (Id₄)

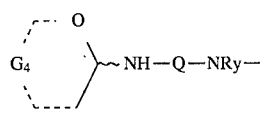
(Id₁)

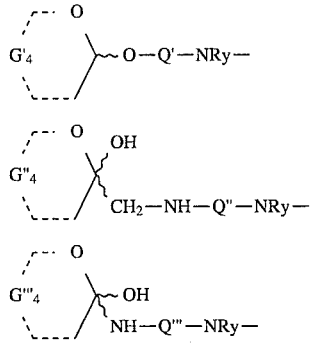
(Id₂)

(Id₃)

(Id₄)

wherein
- Ry is as defined above,
- Q, Q', Q" and Q''' are groups coupling the peptide with the sugar residue, e.g. Q is preferably $-C_bH_{2b}$-CO-(b is 1 to 6) or CO or CS, Q' is preferably $-C_bH_{2b}$-CO-, the radical of a dicarboxylic acid or a residue

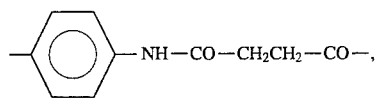

each of —NHQ''' and —NHQ'' is preferably the radical of a ω-aminocarboxylic acid, and $G_4$, $G'_4$, and $G'''_4$ have the definitions given above for $G_1$ or $G_2$;

E) a residue of formula (Ie₁) or (Ie₂)

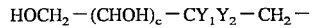
(Ie₁)

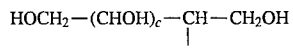
(Ie₂)

wherein
- $Y_1$ and $Y_2$ are as defined above, and
- c is 2, 3 or 4.

By Amadori sugar residue as may be present in the LHRH antagonists of the invention in position 8 is to be understood a sugar residue obtainable by means of an Amadori or Heyns rearrangement, for example a residue of formula (Ia) or (Ib), e.g. of formula (Ia₁), (Ia₂), (Ib₁) or (Ib₂) or of formula (Id₃) or (Id₄) as indicated above. In the Amadori sugar residue of formula (Id₃) or (Id₄), -NH-Q"- or -NH-Q'''- is preferably a -NH-$C_bH2_b$-CO-radical wherein b is preferably an integer from 1 to 3.

In addition to the Amadori sugar residue in 8 position, or to the residues (b₁) and/or (b₂), the LHRH antagonists of the invention may bear one or two sugar residues of formula (Ia) to (Id) above, e.g. in position 1 and/or in position 5 and/or in position 6. Preferably the LHRH antagonists of the invention bear either one Amadori sugar residue in 8 position and a second Amadori sugar residue in 6 position, or one residue of formula (b₁) or (b₂) in 8 position and optionally a second residue of formula (b₁) or (b₂) in 6 position, or two residues of formula (b₁) and/or (b₂) in 8 position and optionally one or two further residues of formula (b₁) and/or (b₂) in 6 position, or one, two or more residues of formula (b₁) or (b₂) on any free amino group in position 1 and/or position 5 and/or position 6.

In the residue of formula (b₁), either g is preferably 0 or g and f are each 0. In the residue of formula (b₂), f is preferably 0.

Residue of formula (b₁) is most preferred.

By the term "physiologically-acceptable ethers" as applied to compounds of the invention containing at least one residue of formula (b₁) or (b₂), is meant ethers in which the hydroxy group(s) in residue (b₁) or (b₂) is(are) etherified and which are not toxic at desired dosage levels. Such ethers include linear, branched or cyclic ethers, e.g. $C_{1-4}$alkyl ethers, for example ethers in which one or all hydroxy present are substituted by methyl, and cyclic ethers in which 2 vicinal hydroxy groups are substituted by e.g

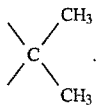

By the term "physiologically-hydrolysable and -acceptable esters" as applied to compounds of the invention containing at least one residue of formula (b₁) or (b₂), is meant esters in which one, two or all hydroxy are esterified and which are hydrolysable under physiological conditions to yield an acid which is itself physiologically acceptable, e.g. non-toxic, at desired dosage levels. Such esters include e.g. esters with aliphatic carboxylic acids having 1 to 6 carbon atoms.

In the compounds of the invention any one of the free hydroxy groups in the residue of formula (b₁) or (b₂) may also be bound in glycosylic manner to a reducing mono-, di- or oligosaccharide or amino sugar.

Depending on the substitution pattern, the residue of formula (b₁) or of formula (b2) may contain one or two asymetric carbon atoms and thus the compounds of the invention may exist in racemic or isomeric form or as diastereoisomers (not taking into account the stereochemistry of the peptidic moiety). Racemic and diastereoisomeric mixtures may be separated into individual isomers in conventional manner. Alternatively optically active starting materials may be employed. The invention covers all forms.

Any $C_{3-5}$alkyl as residue e) may be linear or branched. Preferred is $C_{3-4}$alkyl, particularly isopropyl.

In accordance with the particular findings of the present invention, the present invention provides in a further aspect:

i) a calcitonin peptide in which at least one of the free amino groups other than the N-terminal amino is formylated, preferably in position 7 and/or 11 and/or position 18 and/or position 24;

ii) a calcitonin peptide in which at least one of the free amino groups is modified by one or two residues of formula (b₁) and/or (b₂), particularly (b₁), preferably in position 11 and/or position 18 and/or position 24;

iii) a calcitonin peptide in which at least one of the free amino groups other than the N-terminal amino is modified by $C_{3-5}$alkyl, preferably in position 11 and/or position 18 and/or position 24;

iv) a calcitonin peptide bearing at least in position 24 a sugar residue a), the sugar residue being attached to the ω-amino group of an ω-amino substituted side chain and optionally in position 11 and/or position 18;

v) a calcitonin peptide in which one, more or all of the free amino groups present in said peptide are modified by a combination selected from formyl, $C_{3-5}$alkyl, residues of formula (b₁), (b₂) and/or (a) as defined above within the invention, preferably in position 11 and/or position 18 and/or position 24, more preferably those modified in positions 11 and 18 by formyl and in position 24 by a sugar residue a) as defined.

All known natural calcitonins are polypeptides containing an amino-acid sequence of 32 amino-acids. They are termed using the IUPAC-IUP method of nomenclature (Biochem. J. (1984) 219, 345–377).

The position of each amino-acid involved in the calcitonin peptide chain is numbered according to the accepted procedure beginning at position 1 for Cys on one end of the chain, and ending with Pro at position 32 at the other end of the chain In the following description, this same numbering system is applied to any peptide chain, even if it contains less than the 32 amino-acid units present in the naturally occurring calcitonins, the position of each omitted amino-acid referring to the original numbering. Thus, in the compounds of the invention, the number 24 refers to the position 24 in the calcitonin peptide chain as indicated above, independently whether the compounds contain 32 amino-acid or fewer amino-acid radicals.

The term calcitonin peptide embraces calcitonins which are naturally occurring (whether extracted from natural sources, cell cultures etc. or produced synthetically) and derivatives and analogues having hypocalcemic activity or calcitonin-like activity. Full length calcitonins may be characterized for example by a bridge generally between positions 1 and 7 of the polypeptide chain. Alternatively or additionally they may be characterized by leucine in position 9, and or glycine in position 28 and/or proline in position 32. Derivatives and analogues of these calcitonins include in particular natural calcitonin structures, wherein one or more amino acid radicals are replaced by one or more other amino acid radicals (natural or synthetic) and/or the S-S bridge is replaced by an alkylene bridge, and/or is opened and/or wherein one or several amino acid radicals have been omitted (desaminoacyl derivatives).

An amino-acid is termed "natural" when it is selected from the range of amino-acids which is provided by the genetic codes of living organisms, and "synthetic" when it is selected from amino-acids outside this range.

Examples of ω-amino substituted side chains present in the 24 position of the calcitonins of the invention include a residue of formula IX $$-NH-\underset{Z}{CH}-CO- \qquad (IX)$$

wherein Z is $-W-NR_cR_d$

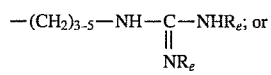

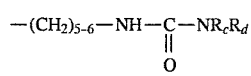

wherein W is arylene, aralkylene or a divalent alicyclic or aliphatic group, preferably phenylene, cyclohexylene or $C_{1-6}$alkylene optionally interrupted by O or S, more preferably $C_{2-5}$alkylene most preferably propyl or butyl;

each of $R_c$ and $R_d$ independently is hydrogen, a sugar residue a), a residue of formula (b₁) or (b₂), formyl or $C_{3-5}$alkyl; $R_e C_{2-5}$alkyl, preferably ethyl.

Preferred calcitonins of the invention are compounds of formula X

wherein o is a whole number from 1 to 5,

R is H or R'CO,

R'CO is the acyl radical of a carboxylic acid, $Y_3$ is the radical located on the α-C-atom of a α-amino acid, $Y_4$ is

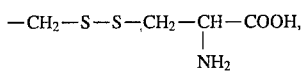

-CH$_2$-S-S-CH$_2$-CH$_2$-COOH, -(CH$_2$)$_5$-COOH, -CH$_2$-S-Y$_5$, or the radical located on the α-C-atom of an α-amino acid (other than those already mentioned),
or one $Y_3$ and $Y_4$ form together a disulphide or tetramethylene bridge when o is 3 or 5, $Y_5$ is alkyl with 1 to 4 C-atoms; benzyl which is optionally substituted by methyl or methoxy; or CH$_3$COHN-CH$_2$-, $A_6$ is Thr or D-Thr, s is a whole number from 3 to 5, $A_8$ is the aminoacyl radical or a neutral, lipophilic L-α-amino acid, $A_9$ is the aminoacyl radical of a neutral, lipophilic L- or D-α-amino acid, $Z_1$ is a polypeptide radical which is located in positions 10 to 23 of a natural calcitonin or a derivative or analogue thereof, which has hypocalcemic activity, and either $Z_3$ is a polypeptide radical which is located in positions 24 to 31 of a natural calcitonin or a derivative or analogue thereof, which has hypocalcemic activity, or $Z_3$ is

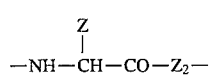 24 wherein

Z is as defined above, and $Z_2$ is a polypeptide radical which is located in positions 25 to 31 of a natural calcitonin or a derivative or analogue thereof, which has hypocalcemic activity, wherein the 1 to 5 $Y_3$ radicals in formula X, independently of one another, may be the same or different, and, with the exception of the aminoacyl radical $A_8$, all amino acid radicals in formula X may have the L- or D-configuration, the compounds of formula X being modified by formyl and/or $C_{3-5}$alkyl on one or several amino groups in one or several side chains, and/or by at least one residue of formula (b$_1$) or (b$_2$) on the N-terminal amino group and/or on one or several amino groups in one or several side chain(s),
with the proviso that $Z_3$ is

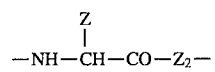 24 wherein Z is -W-NR$_c$R$_d$ when the compound of formula X is modified in 24 position by at least one sugar residue a), in free form or in salt or complex form.

In formula X, $Z_1$ signifies a peptide radical, e.g. known from positions 10 up to 23 and $Z_3$ a peptide radical e.g. known from positions 24 to 31 or 25 to 31 respectively in various known calcitonins, e.g. in human, salmon, eel, chicken, beef, sheep, rat or porcine calcitonin, as well as in derivatives and analogues of the calcitonins, having similar biological activity. These peptide radicals $Z_1$, $Z_2$ and $Z_3$ may normally comprise each 14, 7 and 8 amino acids respectively, but they may also contain a correspondingly smaller number of amino acid radicals by omitting one or several amino acid radicals (des-aminoacyl derivatives).

$Z_1$ preferably denotes a) Gly-Lys-Leu-Ser-Gln-Glu-Leu-His-Lys-Leu-Gln-Thr-Tyr-Pro-, in which case $Z_3$ is -Arg-Thr-Asp-Val-Gly-Ala-ly-Thr or

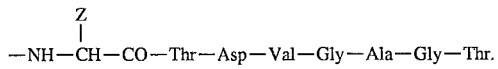

b) Gly-Lys-Leu-Ser-Gln-Glu-Leu-His-Lys-Leu-Gln-Thr-Tyr-Pro-, in which case $Z_3$ is -Arg-Thr-Asn-Thr-Gly-Ser-Gly-Thr or

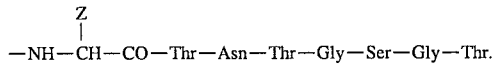

In $Z_1$ a preferred amino-acid radical in the position 10 may also be Aib (aminoisobutyric acid radical) or DAla.

A preferred amino-acid radical in the position 17 in $Z_1$ may also be Aib.

R'CO is preferably HCO or the acyl residue of an aliphatic, cycloaliphatic, aromatic or heterocyclic carboxylic acid.

R' is preferably a') hydrogen or a saturated or unsaturated, straight-chain or branched alkyl with 1 to 17 C-atoms, especially saturated alkyl with 3 to 9 C-atoms, b') cycloalkyl with 5 to 7 C-atoms or cycloalkylakyl wherein the cycloalkyl group contains 5 to 7 C-atoms and the alkyl radical contains 1 to 2 C-atoms, c') adamantyl, adamantylmethyl or adamantylethyl, or d') phenyl, benzyl or phenethyl.

In the above-mentioned definitions for R', the alkyl, cycloalkyl or phenyl radicals may be substituted by the usual substituents, e.g. by halogen, NO$_2$, OH, alkoxy, etc.

The residue R'CO may be e.g. the α-desamino residue of a natural or synthetic α-amino acid. For R', definitions a'), b') and c') are preferred.

$Y_3$ and $Y_4$ as radicals which are found on the α-C-atom of an α-amino acid are in particular the radicals which are bonded to the α-C-atom of a natural α-amino acid, but radicals of other α-amino acids may also be contemplated, e.g. of 3-cyclohexyl-alanine or of α-aminoisobutyric, α-aminobutyric acid or of (L-)-α-aminosuberic acid.

when o in formula X signifies 5, $Y_3$ on the N-terminal (position 1) and $Y_4$ in position 7 preferably form together a disulphide or tetramethylene bridge or each of $Y_3$ in position 1 and $Y_4$ is -(CH$_2$)$_5$-COOH or a derivative thereof. The second to fifth $Y_3$ have preferably each a significance as indicated thereafter when o=4.

When o signifies 4, a) the N-terminal aminoacyl radical (corresponding to the second amino acid radical in the sequence of the natural calcitonins) is preferably Ser, Gly or Ala, b) the second aminoacyl radical (corresponding to the third amino acid radical in the sequence of the natural calcitonins) is preferably Asn or Ser, c) the third aminoacyl radical (corresponding to the fourth amino acid radical in the sequence of the natural calcitonins) is preferably Leu, Asn, Ser, Phe, D-Leu or the radical of cyclohexylalanine, d) the fourth aminoacyl radical (corresponding to the fifth amino acid radical in the sequence of the natural calcitonins) is preferably Ser or Ala.

When o in formula X is 3, the N-terminal, the second and the third amino acid radicals have the same preferred definitions as above for the case when o=4 under b). $Y_3$ on the N-terminal and $Y_4$ may also form together a disulphide or tetramethylene bridge. When o in formula X is 2, the N-terminal and the second amino acid radicals have the same preferred definitions as above for the case when o=4 under c) and d).

When o in formula X is 1, the N-terminal and the second amino acid radical is preferably Ser or Ala.

$A_6$ is preferably Thr;

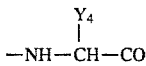

preferably denotes Cys, a derivative of cystein as given above for $Y_2$, or a neutral lipophilic α-amino-acyl radical, especially Ala or another neutral lipophilic α-aminoacyl radical, in particular Ala;

when

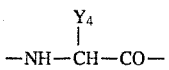

is in 7 position, it may also be a residue of formula IX as defined above, Orn, Lys or Orn or Lys substituted in $N^d$ or $N^e$ respectively by $C_{1-6}$alkanoyl;

$A_8$ is preferably the aminoacyl radical of a neutral lipophilic α-amino acid, especially Val or Gly, $A_9$ is also preferably the aminoacyl radical of a neutral lipophilic α-amino acid, especially Leu or Phe.

In the compounds of formula X, o is preferably 2, wherein R signifies H or R'CO, or in particular, o is 1 and R is R'CO.

All the amino acid radicals preferably have L-configuration.

The natural luteinizing hormone releasing hormone LHRH is a decapeptide comprised of naturally occurring amino-acids. LHRH antagonists include analogues and derivatives thereof wherein one or more amino-acid radicals have been omitted and/or replaced by one or more other amino-acid radicals and/or wherein one or more functional groups have been replaced by one or more other functional groups and/or wherein one or more groups have been replaced by one or several other isosteric groups and/or wherein the C-terminal sequence has been modified.

Examples of ω-amino substituted side chain in 8 position of the LHRH antagonists of the invention include side chains in which the ω-amino group is bound in the alpha position of the amino-acid unit in 8 by a bridging member. The bridging member may e.g. have one of the significance given above for W.

Preferred LHRH antagonist peptides of the invention are compounds of formula XI $$R_1-A_1-B_1-C_1-D_1-E_1-F_1-G_1-H_1-I_1-K_1-NH_2 \qquad (XI)$$

wherein $R_1$ is hydrogen, $C_{1-7}$acyl, carbamoyl, a sugar residue a) or a residue (b) or ($b_2$)

$A_1$ is D-Phe optionally substituted in the phenyl ring by halogen, $CF_3$, $C_{1-3}$alkyl and/or $C_{1-3}$alkoxy, α- or β-naphtyl-D-alanine, D-Trp optionally substituted in 5 or 6 position by halogen or $C_{1-3}$alkoxy and/or in 1 position by formyl or acetyl, D- or L-Pro, D- or L-3,4-dehydroproline, D- or L-Ser, D- or L-Thr, D- or L-Ala, D-pyroglutamine, 3-(9-anthryl)-D,L-alanyl, 3-(2-fluorenyl)-D,L-alanyl or 3-(Het)-D,L-alanyl wherein Het is a heterocyclic aryl radical selected from

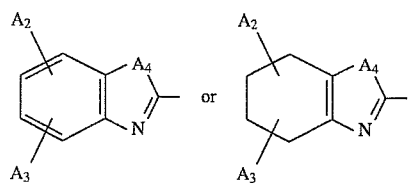

wherein $A_2$ and $A_3$ are independently selected from the group consisting of hydrogen, $C_{1-4}$alkyl, chlorine and bromine, and $A_4$ is O, S or N $B_1$ is D-Phe optionally substituted in the phenyl ring by halogen, $NO_2$, $C_{1-3}$alkyl or $C_{1-3}$alkoxy, D-α-methylPhe optionally substituted in 4 position by chlorine, 2,2-diphenylglycine or 3-(2-naphthyl)-D-alanine, $C_1$ is D-Trp optionally substituted in 5 or 6 position by halogen, $NO_2$ or $C_{1-3}$alkoxy and/or in 1 position by formyl or acetyl, 3-(2- or 1-naphthyl)-D-alanine, 3-D-pyridylalanine, D-Tyr, D-Phe optionally substituted by halogen, $C_{1-3}$alkyl and/or $C_{1-3}$-alkoxy, D-3-Pz-Ala, D-Tin-glu or D-Nic-Lys, $D_1$ is L-Ser, $E_1$ is Tyr, Phe optionally substituted in the phenyl ring by halogen, $C_{1-3}$alkyl and/or $C_{1-3}$alkoxy, Orn, Lys, Lys-Nic, MPic-Lys, Lys-Pic, Mpic-Lys, DMG-Lys, Pmc-Lys, Pzc-Lys, His, Dpo, Arg, 3-3-pyridyl)-Ala, Trp, N-(3-pyridyl)acetyl-Lys or Glu(pMeO-phenyl), Cit, HOBLys or PzACAla, the free amino group present in said amino-acid units being optionally substituted by a sugar residue a) or at least one residue ($b_1$) or ($b_2$)

$F_1$ is d-Phe optionally substituted in the phenyl ring by halogen, $NO_2$, $C_{1-3}$alkyl or $C_{1-3}$alkoxy, D-Trp optionally substituted in 5 or 6 position by halogen, $NO_2$ and/or $C_{1-3}$alkoxy and/or in 1 position by formyl or acetyl, 3-(2-naphthyl)-L-alanyl, D-Tyr, D-Lys-Nic, D-MNic-Lys, D-MPic-Lys, D-Pmc-Lys, D-Pzc-Lys, D-Bz-Lys, D-ILys, AnGlu, D-NaCAla, D-PzACAla, D-PmACAla, D-3-(3-pyridyl)-Ala, D-His (subst. H or benzyl), D-Arg, D-homo-Arg($Et_2$), D-cit, D-HCi, D-Lys-Pic, D-Cit($C_{1-3}$alkyl), D-HCi($C_{1-3}$alkyl), D-Glu(AA) or α-amino-ω-ureido-$C_{2-4}$alkanoic acid, the free amino group present in said amino-acid units being optionally substituted by a sugar residue a) or at least one residue ($b_1$) or ($b_2$) or a residue

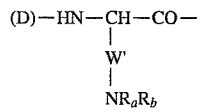

wherein W' is $C_{1-6}$alkylene, methoxy-$C_{1-4}$alkylene, methyl-thio-$C_{1-4}$ alkylene or cyclohexylene, each of $R_a$ and $R_b$ independently is hydrogen, a sugar residue a), a residue of formula ($b_1$) or ($b_2$) or one of $R_a$ and $R_b$ is hydrogen and the other is $C_{2-5}$alkanoyl, benzoyl or phenylpropionyl, $G_1$ is Leu, Nle, Nval, N-α-methylLeu, Trp, Phe, Met, Tyr, Val, Ile, alloIle, Abu, Ala or

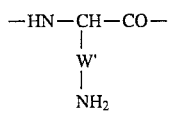

wherein
W' is as defined above,
$H_1$ is

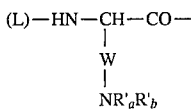

wherein W is as defined above, preferably phenylene, cyclohexylene or has the definition of W' above, each of $R'_a$ and $R'_b$ independently is hydrogen, an Amadori sugar residue, preferably of formula $(Ia_1)$, $(Ia_2)$, $(Ib_1)$, $(Ib_2)$, $(Id_3)$ or $(Id_4)$, or a residue of formula $(b_1)$ or $(b_2)$, Arg, IOrn, ILys or Cyp-Lys $I_1$ is Pro, hydroxyproline, 3,4-dehydroproline, Pip and $K_1$ is D-Ala, D-Leu, Gly, D-Ser or Sar, in free form or in salt or complex form.

In the LHRH antagonists of the invention, the following significances are preferred either individually or in any combination or sub-combination:

$R_1$ is acetyl;

$A_1$ is D-Phe, D-Phe(p-Cl), D-Phe(p-F), $Cl_2$-Phe or D-2-Nal;

$B_1$ is D-Phe, D-Phe(p-cl) or D-Phe(p-F);

$C_1$ is D-Trp, D-2-Nal, D-3-Pal or D-Phe;

$D_1$ is Ser;

$E_1$ is Tyr, Nic-Lys, MNic-Lys, Pic-Lys, Pzc-Lys, Arg, 3-Pal, Orn, Lys or Orn or Lys substituted on the side chain amino group by an Amadori sugar residue as defined above or by at least one residue of formula $(b_1)$ or $(b_2)$;

$F_1$ is D-3-Pal, DPhe, D-Orn, D-Lys, D-His (subst. H or benzyl), D-Nic-Lys, D-MNic-Lys, D-Pic-Lys, D-Pz-cLys, cis-D-PzACAla, D-Trp, D-Tyr, D-2-Nal, D-Arg, D-Cit, D-HCi, D-homoArg-($Et_2$) or D-Orn or D-Lys substituted on the side chain amino group by an Amadori sugar residue as defined above or by at least one residue of formula $(b_1)$ or $(b_2)$;

$G_1$ is Leu, Nle, Val or Phe;

$H_1$ is

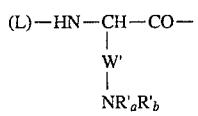

wherein W' is as defined above, each of $R'_a$ and $R'_b$ independently is hydrogen, an Amadori sugar residue of formula $(Ia_1)$ $(Ia_2)$, $(Ib_1)$, $(Ib_2)$, $(Id_3)$ or $(Id_4)$, or a residue of formula $(b_1)$ or $(b_2)$;

$I_1$ is Pro;

$K_1$ is D-Ala, D-Ser or Gly.

It is understood that when the compounds of formula X or XI comprise at least one residue of formula $(b_1)$ or $(b_2)$, such include also the physiologically-acceptable ethers and the physiologically-hydrolysable and -acceptable esters thereof as indicated above.

Throughout the present specification and claims, by "halogen" is preferably meant fluorine, chlorine or bromine.

The compounds of formula I may exist e.g. in free form, in salt form or in the form of complexes thereof. Acid addition salts may be formed with e.g. organic acids, polymeric acids and inorganic acids. Such acid addition salt forms include e.g. the hydrochlorides and acetates. Complexes are formed from compounds of formula I on addition of inorganic substances, e.g. inorganic salts or hydroxides such as Ca- and Zn-salts, and/or on addition of polymeric organic substances.

The present invention in another aspect provides a process for the production of compounds of the invention, comprising i) removing the protecting group or groups from a protected polypeptide according to the invention, ii) for the preparation of the compounds of the invention bearing at least one residue of formula $(b_1)$ or $(b_2)$, reductively aminating a compound of formula III

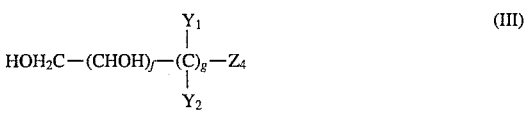

wherein

| | |
|---|---|
| f | is as defined above |
| either g | is 0 or 1, |
| $Y_1$ and $Y_2$ | have one of the significances given above and |
| $Z_4$ | is —CHO, |
| or g | is 1, |
| $Z_4$ | is $CH_2OH$ and $-CY_1Y_2-$ form together carbonyl, | and the free hydroxy groups thereof may be etherified or esterified,
with a compound of formula IV

P-$NH_2$      IV wherein P is a calcitonin peptide residue or LHRH antagonist residue in which the free amino groups are in protected form
and, if necessary, carrying out process step i);

iii) for the preparation of calcitonin compounds comprising at least one formyl or $C_{3-5}$alkyl attached to an amino group other than a N-terminal amino group, reacting a compound of formula IV as defined above with a compound of formula V

$Z_5$-CHO      V wherein $Z_5$ is hydrogen or $C_{3-5}$alkyl, or with a chloroformate and, if necessary, carrying out process step i);

iv) coupling together by an amide bond two peptide fragments, each of which contains at least one amino acid in protected or unprotected form and one peptide fragment containing a residue a) to f) as defined above, the peptide fragments being such that a protected or unprotected polypeptide having the sequence according to the invention is obtained and, if necessary, carrying out process step i);

v) removing or converting a functional group of an unprotected or a protected polypeptide into another functional group so that an unprotected or a protected polypeptide is obtained, and in the latter case stage i) of the process is effected;

vi) for the preparation of a calcitonin or LHRH antagonist peptide comprising at least one sugar residue a) introducing at least one optionally protected sugar residue into a protected or unprotected peptide and if necessary carrying out process step i);

vii) separating optically active isomers from any mixture of such isomers obtained in accordance with steps (i) to (vi);

and recovering a compound thus obtained in free or salt form or in the form of a complex.

The above process may for example be carried out analogously to the processes described in the accompanying examples.

Process steps i), iv), v) and vii) may be carried out by methods known in the art of peptide chemistry.

Where desired, in these reactions, protecting groups which are suitable for use in peptides or sugars may be used for functional groups which do not participate in the reaction. The term protecting group may also include a polymer resin having functional groups.

Process step ii) may be effected in a conventional manner for the reductive amination of an aldose or ketose. It may be performed for example in the presence of $NaBH_3CN$, preferably at an acidic pH, e.g. from pH 5 to 7. The temperature of the reaction may be e.g. from room temperature to 100° C. It may be advantageous to carrying out the reaction in an inert solvent, e.g. water, an alcohol, dioxane or DMF or a mixture thereof.

Process step iii) may be carried out in a conventional manner, as used e.g. for formylation or for reductive alkylation. It may be performed for example in the presence of $NaBH_3CN$, preferably at an acidic pH, and at temperature and solvent conditions e.g. such as disclosed above for process step ii).

The compounds of the invention or a peptide fragment bearing a sugar residue of formula (Ia) may be produced by reacting a protected peptide or peptide fragment having a free amino group in a slightly acidic medium with a reducing mono-, di- or oligosaccharide or a corresponding uronic acid or ester thereof (Amadori rearrangement), and subsequently optionally removing the protecting group.

This reaction may take place in a conventional manner for the Amadori rearrangement. The acid added may be e.g. glacial acetic acid. When reacting with uronic acid, an additional acid may be dispensed with. It is preferred to use an excess of carbohydrate, e.g. ten equivalents for one equivalent of peptide compound. The reaction may be carried out in a polar solvent such as methanol, preferably at temperatures of ca. 50° C. to 70° C.

The compounds of the invention or a peptide fragment bearing a sugar residue of formula (Ib) may be produced by reacting a protected peptide or peptide fragment having a free amino group in a slightly acidic medium with a ketose (Heyns rearrangement). The reaction can be carried out under the same conditions as for the Amadori rearrangement (see above).

The compound of the invention or a peptide fragment bearing a sugar residue of formula (Ic) can be produced by reacting a protected peptide or peptide fragment having a free amino group with an acid of formula $G_3$-COOH or a reactive derivative of such an acid, and then optionally removing the protecting group(s). This may be a conventional amidation reaction, which can be effected in known manner. The amides can e.g. preferably be produced with the free acids in the presence of hydroxybenotriazole and dicyclohexylcarbodiimide.

The compounds of the invention or a peptide fragment bearing a sugar residue of formula ($Id_1$), ($Id_2$), ($Id_3$) or ($Id_4$) may be produced by a) reacting the peptide or peptide fragment first of all with the bridge member and then reacting the product with the sugar, or b) reacting the sugar first of all with the bridge member and then reacting the glycated bridge member with the peptide or peptide fragment.

These reactions may be effected in conventional manner.

Compounds of the invention or a peptide fragment bearing a sugar residue of formula ($Id_1$) wherein Q is -CO- or -CS- may be produced for example by coupling the corresponding glycosylisocyanate or glycosylisothiocyanate of formula

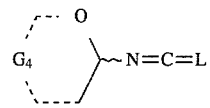

wherein L is O or S, and $G_4$ is as defined above and wherein the free hydroxyl groups present in $G_4$ are protected, e.g. by acylation, to a protected peptide or peptide fragment with a free amino group, and thereafter splitting off the protecting groups.

This reaction may be effected in conventional manner for the production of urea derivatives.

Compounds of the invention or a peptide fragment bearing a sugar residue of formula ($Id_3$) or ($Id_4$) may be obtained by means e.g. of an Amadori or Heyns rearrangement, e.g. as described above for the production of compounds bearing a sugar residue of formula (Ia) or (Ib).

A compound of the invention or a peptide fragment bearing a sugar residue of formula ($Ie_1$) or ($Ie_2$) may be produced e.g. by a') reductive amination of an aldose, deoxyaldose or ketose with the peptide or peptide fragment bearing a free amino group, e.g. as disclosed above in step ii), or b') reducing the hemi-acetal group in a compound bearing a sugar residue of formula (Ia) or (Ib), wherein if desired any reactant may be temporarily protected.

The peptide fragment containing a residue a), ($b_1$) or ($b_2$) used as starting material in process step iv) above may be prepared employing a "building stone", e.g. a corresponding α-amino-acid substituted on the side chain amino group by said residue, preferably a Lys or Orn unit substituted in $N^\epsilon$ or $N^d$ respectively by a sugar residue a) or preferably by one or two residues of formula ($b_1$) or ($b_2$). Such a building stone may be prepared by reacting the corresponding amino-acid (or peptide fragment) in protected form analogously to known methods, e.g. by reductive amination for the introduction of the residues of formula ($b_1$) or ($b_2$), for example as disclosed above or below in the accompanying Examples. The building stone can be used for peptide synthesis in solution or solid phase production process.

The calcitonin peptides bearing in 24 position an α-amino acid residue

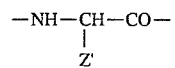

wherein Z' is W-$NH_2$, particularly a ω-amino-$C_{1-6}$alkyl residue, in free form or salt or complex form, and used as starting materials, e.g. in process step (ii) or iii), are novel and form also part of the invention. These peptides can be produced by methods which are generally known for the synthesis of compounds of this kind, e.g. in solution or by the solid phase process.

Insofar as the production of the starting materials is not particularly described, the compounds are known or may be produced and purified in accordance with methods known in the art.

In the following examples all temperatures are in °C. and $[\alpha]_D^{20}$-values are uncorrected. The following abbreviations are employed.

BOC=tert.-butyloxycarbonyl
DMF=dimethylformamide
MeOH=methanol
AcOH=acetic acid
Bu$^t$=tert.butyl
Fmoc=9-fluorenylmethoxycarbonyl
DCM=Dichloromethane
Abu=2-aminobutyric acid
AnGlu=4-(4-methoxyphenylcarbamoyl)-2-aminobutyric acid
BzLys=N$^\epsilon$-benzoyllysine
Cit=citrulline=2-amino-5-ureidopentanoic acid
HCi=homocitrulline=2-amino-6-ureidohexanoic acid
CypLys=N$^\epsilon$-cyclopentyllysine
DMGLys=N$^\epsilon$-(N,N-dimethylglycyl)lysine
HOBLys=N$^\epsilon$-(4-hydroxybenzoyl)lysine
Ilys=N$^\epsilon$-isopropyllysine
IOrn=N$^d$-isopropylornithine
MNicLys=N$^\epsilon$-(6-methylnicotinoyl)lysine
MPicLys=N$^\epsilon$-(6-methylpicolinoyl)lysine
NACAla=3(4-nicotinoylaminocyclohexyl)alanine
2-Nal=3-(2-naphthyl)alanine
NicLys=N$^\epsilon$-nicotinoyllysine
NicOrn=N$^d$-nicotinoylornithine
Nle=norleucine, 2-aminohexanoic acid
NMeLeu=N-methylleucine
Nval=norvaline, 2-aminopentanoic acid
3-Pal=3-(2-pyridyl)alanine
pClPhe=3-(4-chloro)phenylalanine
PicLys=N$^\epsilon$-picoloyllysine
Pip=piperidine-2-carboxylic acid
PmcLys=N$^\epsilon$-(4-pyrimidinylcarbonyl)lysine
PmACAla=3[4(4-pyrimidinylcarbonyl)aminocyclohexyl]alanine
PzACAla=3(4-pyrazinylcarbonylainocyclohexyl)alanine
3-PzAla=3-pyrazinylalanine
PzcLys=N$^\epsilon$-pyrazinylcarbonyllysine
Sar=N-methylglycine
TinGly=3-thienylglycine
(AA)=p-methoxy-phenyl All peptides are obtained as a polyacetate polyhydrate except where otherwise stated with a peptide content of from 70 to 90%. The polypeptides contain less than 5% of other peptides by HPLC-analysis.

"F" as used herein after refers to the proportion of polypeptides (=peptide content) in the preparations obtained (F=1 corresponds to 100 per cent), the difference to 100% is made of acetic acid and water.

EXAMPLE 1

CH$_3$CO-D-2-Nal-DPhe(p-Cl)-DTrp-Ser-Tyr-DLys(CH$_2$-CHOH-CH$_2$OH)-Leu-Lys(CH$_2$-CHOH-CH2OH)-Pro-DAla-NH$_2$ 300 mg CH$_3$CO-D-2-Nal-DPhe(p-Cl)-DTrp-Ser-Tyr-DLys-Leu-Lys-Pro-DAla-NH$_2$ and 90 ml D-(+)-glycerinaldehyde are dissolved in MeOH in the presence of sodium phosphate buffer at pH6. A total of 260 mg NaCNBH$_3$ is then added, the pH of the resulting mixture kept at 5–6 by addition of 10% H$_3$PO$_4$ and the whole is stirred at room temperature overnight. Afterwards the reaction mixture is diluted with water and the pH is adjusted to 8–9 by addition of 1N ammonium hydroxide. The slightly turbid solution is slowly filtered on a Duolite column and the column is rinsed with water. The absorbed product is then eluted with a mixture of dioxan/water/AcOH and the resulting eluate is concentrated in vacuo, diluted with water and lyophilised. The resulting raw product is purified 1. by chromatography on silicagel with a mixture of CHCl$_3$/MeOH/AcOH/water and 2. by HPLC on a RP-18 column (Acetonitrile-2% H$_3$PO$_4$). The fractions which contain the title compound are collected and filtered on an ion exchange resin (AG3-X4) in acetate form. The title compound, is concentrated in vacuo, diluted with water and lyophilised.

$[\alpha]_D^{20}$=–34° (c=0.1 in 95% AcOH), F=0,83.

EXAMPLE 2

CH$_3$CO-DPhe(p-Cl)-DPhe(p-Cl)-DTrp-Ser-Tyr-DLys(R$_2$)-Leu-Lys(R$_2$)-Pro-DAla-NH$_2$

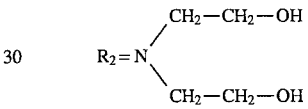

420 mg CH$_3$CO-DPhe(p-Cl)-DPhe(p-Cl)-DTrp-Ser-Tyr-DLys-Leu-Lys-Pro-DAla-NH$_2$ are dissolved in a mixture of 15 ml MeOH and 15 ml 0.1M sodium phosphate buffer at pH 5.5 and placed under argon atmosphere. 300 mg glycolaldehyde and a total of 720 mg NaCNBH$_3$ are then added thereto and the resulting mixture is stirred for 1 hour at room temperature and then for about 15 hours at 50° C. Thereafter the pH of the mixture is adjusted to 2 by addition of 1N HCl and the mixture is stirred for about 1 hour at pH 2. The pH is then adjusted to about 7 by addition of 1N ammonium hydroxide. After dilution with water and a small amount acetonitrile, the mixture is placed on a Reversed Phase (RP)-18 HPLC column (for example organic HDSIL-18-10-100). The adsorbed product is eluted by means of an acetonitrile gradient in 2% H$_3$PO$_4$ from the RP-18 column. The fractions which contains the title compound are collected, filtered on a slightly basic ion exchange resin in acetate form (BioRad AGX4, acetate). The eluate is concentrated in vacuo, the residue diluted with water and then lyophilised. The resulting title compound has $[\alpha]_D^{20}$=–20° (c=1 in 95% AcOH)

EXAMPLE 3

CH$_3$CO-D-2-Nal-DPhe(p-Cl)-DTrp-Ser-Tyr-DTrp-Leu-Lys(CH$_2$-CHOH-CH$_2$OH)-Pro-DAla-NH$_2$

The procedure of Example 1 is repeated.

$[\alpha]_D^{20}$ =33° (c=0.1 in 95% AcOH).

EXAMPLE 4

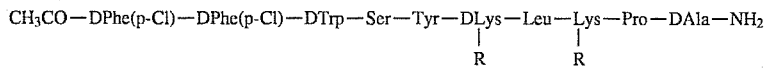

R=N^ε-1-desoxy-fructosyl 120 mg CH₃CO-DPhe(p-Cl)-DPhe(p-Cl)-DTrp-Ser-Tyr-DLys-Leu-Lys-Pro-DAla-NH₂ and 310 mg D(+)glucose in 24 ml DMF/AcOH 15:1 are stirred at 55° C. for 4 hours. The reaction mixture is precipitated with ether and filtered. The residue is dissolved in water, adjusted to pH 7–7.5 with diluted ammonium hydroxide and then purified by adsorption on Duolite ES 861 and elution with H₂→dioxane-H₂O-AcOH (gradient). The eluate is concentrated in vacuo and then lyophilized.

The lyophilisate is purified by 1) chromatography on a silica gel column using as eluant CHCl₃/MeOH/AcOH/H₂O or reversed phase chromatography on an octadecyl-silica gel column;
2) adsorption on Duolite ES 861 and elution with a mixture of dioxan/water/AcOH as disclosed above.

Fractions which contain the title compound are collected, concentrated and lyophilised, this giving the title compound.

$[\alpha]_D^{20} = -37°$ (c=0.5 in 95% AcOH)

EXAMPLE 5

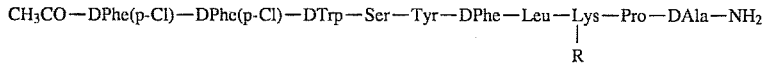

R=N^ε-1-desoxyfructosyl

The title compound is produced in analogous manner to that described in Example 1.

$[\alpha]_D^{20} = -34°$ (c=0.5 in 95% AcOH).

EXAMPLE 6

By repeating the procedure of Example 4, the following compounds are obtained:

CH₃CO-A-DPhe(p-Cl)-DTrp-Ser-Tyr-F-Leu-H-Pro-DAla-NH₂

| | A | F | H | R |
|---|---|---|---|---|
| a) | D-2-Nal | DTrp | Lys(R) | (N^ε-1-Desoxyfructosyl) $[\alpha]_D^{20} = -32.4°$ (c = 0.5 in 95% AcOH) |
| b) | D-2-Nal | DLys(R) | Lys(R) | (N^ε-1-Desoxyfructosyl) $[\alpha]_D^{20} = -38.6°$ (c = 0.5 in 95% AcOH) |
| c) | D-p-Cl-Phe | DLys(formyl) | Lys(R) | (N^ε-1-Desoxyfructosyl) $[\alpha]_D^{20} = -32°$ (c = 0.25 in 95% AcOH) |

The starting materials used in the Examples above may be produced in analogy with the procedure disclosed e.g. in U.S. Pat. No. 4,628,044.

EXAMPLE 7

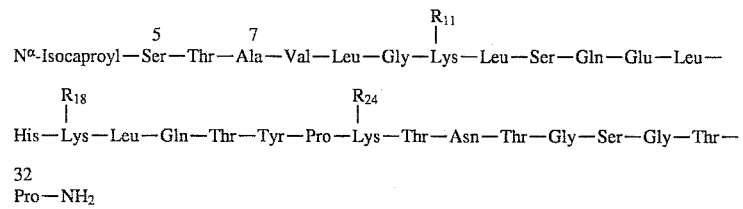

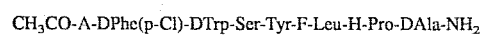

R=N^ε-1-deoxyfructosyl 10.3 g of N^α-isocaproyl-des(1-4)-[Ala⁷, Lys²⁴]salmon calcitonin polyacetate and 1.8 g of D(+)-glucose are dissolved in a mixture of 94 ml of DMF and 6 ml of acetic acid. After 2 hours at 50° C., the product is completely precipitated by adding ether, then filtered off by suction, washed with ether and vacuum-dried. Purification is effected by dissolving ca. 5–10 g of the product in water, loading the solution into a reversed-phase column, 4×25 cm of C-18 on silicagel and chromatographing with a gradient of water and 0–80% of a solvent mixture comprising 38 parts of water, 60 parts of acetonitrile and 2 parts of 85% phosphoric acid. The fractions which contain the pure product are combined, filtered over a column containing ca. 100 ml of a slightly basic ion exchanger in the acetate form and washed with water. The filtrate is lyophilised and the title compound is obtained as the polyacetate, polyhydrate.

$[\alpha]_D^{20}=-36.8°$ (c=0.3 in CH$_3$COOH 95%), F=0.73

FAB mass spectroscopy (MH$^+$)=3541.
The starting product may be produced as follows:

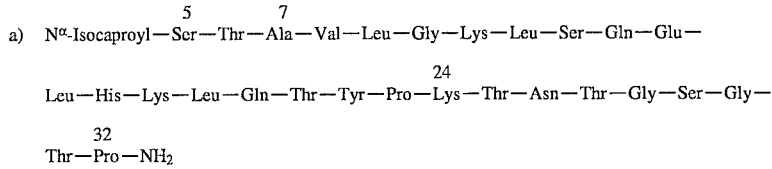

This peptide is assembled in a stepwise manner on a poly-styrene-based resin support. The Boc-group is used for protection of the alpha amino-groups and side-chain functional groups are protected as Lys(2-chlorobenzyloxy-carbonyl), Ser(benzyl), Thr(benzyl), His(tosyl), Tyr(4-bromobenzyloxycarbonyl), Cys(4-methylbenzyl), Glu(benzyl).

Amino-4-methylphenyl-methyl-co(polystyrene-divinylbenzene=MBHA-resin) (0.7 mmol/g) is subjected to the following cycle, steps (1) to (7), of treatments:

(1) DCM
(2) trifluoracetic acid (50%) in DCM
(3) DCM
(4) diisopropylethylamine (10%) in DMF
(5) DMF
(6) preformed symmetrical anhydride (2,8 mmol per g starting resin) of Boc-amino acid in DMF
(7) DMF Volumes of washes and reagents are 5 to 20 ml per gram of starting resin.

Each step is repeated as many times as necessary for either complete reaction of the resin (steps 2, 4, 6) or complete displacement of the previous reagent from the resin (steps 1, 3, 5, 7). Samples of resin are taken after each cycle and checked for completeness of reaction by a ninhydrin-test.

Symmetrical anhydrides of Boc-amino acids are formed just prior to use by reacting Boc-amino acid (2,8 mmol per g resin) and DCCI (1,4 mmol per g resin) in DCM, containing DMF in amounts sufficient for complete dissolution of the Boc-amino acid. The mixture is filtered, more DMF is added to the filtrate, concentrated by evaporation of the volatile components at a temperature not exceeding 15° C. and the resulting solution is used in step (6).

The cycle of reactions, (1) to (7), is repeated for each amino acid residues such as to provide the sequence of formula I, except for Boc-Gln-OH and Boc-Arg(Tos)-OH which are coupled in step (6) as their preformed 1-hydroxybenotriazole estersin DMF.

In the last cycle, in step (6), isocaproic acid, diisopropylcarbodiimid and 1-'hydroxybenzotriazol (all at 3.5 mmol per g of starting resin) in DMF are added to the resin. After 15 hours, the resin is washed with DMF and DCM and dried.

To the peptide resin (1 g) are added p-cresol (1 g), dimethylsulfide (1 ml) and HF (10 ml). After 1 hour at 0° C., the volatile components are distilled off at 0° C. The residue is washed with ethyl acetate and extracted with several portions of acetic acid (10%) in water and the aqueous extract lyophilized. The lyophilized product is purified by reversed-phase chromatography on a column of octadecyl-silica and eluted with a gradient of acetonitril in phosphoric acid (2%). Fractions containing the compound in pure form are combined, filtered through a weakly basic ion-exchange resin in the acetate form, and the filtrate lyophilized.

The title compound a) as the polyacetate, polyhydrate is obtained as a white, fluffy powder.

$[\alpha]_D^{20}=-34.3°$ (c=0.26 in CH$_3$COOH 95%), F=0.78

FAB mass spectrocopy (MH$^+$)=3054

EXAMPLE 8

N$^\alpha$-Fmoc-N$^\epsilon$-2,3-0,0'-isopropyliden-2,3-dihydroxy-(2S)-propyl-lysin 4 g Fmoc-Lys-OH,HCl are dissolved in 80 ml MeOH/H$_2$O and the pH is then adjusted to 5 by means of a phosphate buffer. After addition of 2.6 g 2,3-0,0'-isopropyliden-D-glycerinaldehyde and 3.1 g NaCNBH$_3$, the resulting mixture is stirred for 5 hours at room temperature. The pH increase which may take place during the reaction is adjusted by addition of 10% H$_3$PO$_4$. When the reaction is complete (TLC), the pH of the mixture is adjusted to 3 with HCl, the mixture is diluted with water and then extracted with a mixture of CH$_2$Cl$_2$/isopropanol (4/1 v/v). After chromatography on silica gel, the title compound is obtained in form of an amorphous product.

$[\alpha]_D^{20}=+0.3°$ (c=1 in DMF)

The following compound may also be obtained as by-product:

N$^\alpha$-Fmoc, N$^\epsilon$, N$^\epsilon$-Bis-(2,3-0,0'-isopropyliden-2,3,dihydroxy-(2S)-propyl)-lysin $[\alpha]_D^{20}=0°$ (c=1 in DMF)

EXAMPLE 9

N$^\alpha$-Fmoc-N$^\epsilon$-2,3,-0,0'-isopropyliden-2,3-dihydroxy-(2S)-propyl-N$^\epsilon$-BOC-lysin 2.4 g of the compound obtained in Example 8 are dissolved in 200 ml DMF/H$_2$O (3/1 V/V) and after addition of 4.3 g NaHCO$_3$, 2.3 g BOC$_2$O are added thereto. After 30 minutes reaction, the mixture is diluted with H$_2$O, the pH is adjusted to 3 with HCl and the mixture is extracted with CH$_2$Cl$_2$. The organic phase is dried, concentrated and the residue purified by chromatography on silica gel (elution with $CH_2Cl_2CH_2Cl_2$/MeOH 8/2), yielding the title compound.

$[\alpha]_D^{20} = 0°$ (c=1 in DMF)

EXAMPLE 10

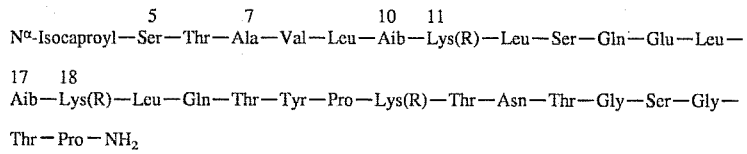

R=$N^\epsilon$-1-deoxyfructosyl

This compound is obtained in analogous manner to Example 7 starting from $N^\alpha$-isocaproyl-des(1-4-[Ala$^7$, Aib$^{10,17}$,Lys$^{24}$]salmon calcitonin.

$[\alpha]_D^{20}=-39.0°$ (c=0.22 in 95% AcOH), F=0.85

FAB-MS: 3516.1 (MH$^+$)
(The preparation of the starting material is described in Example 16).

EXAMPLE 11

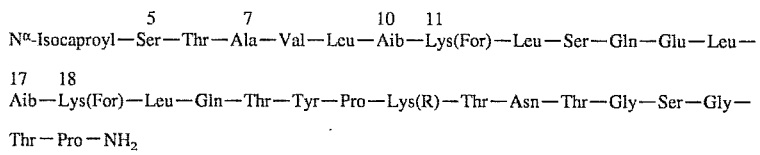

R=$N^\epsilon$-1-deoxyfructosyl

This compound is prepared in analogous manner to Example 7 starting from $N^\alpha$-isocaproyl-des(1-4)-[Ala$^7$, Aib$^{10,17}$Lys(For)$^{11,18}$, Lys$^{24}$]salmon calcitonin.

$[\alpha]_D^{20}=-60.7°$ (c=0.29 in 95% AcOH), F=0.90

FAB-MS: 3280 (MH$^+$)
(The preparation of the starting material is described in Example 24).

EXAMPLE 12

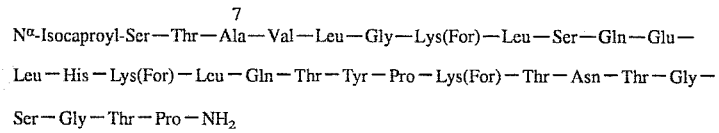

80 mg of $N^\alpha$-Isocaproyl-des(1-4)-[Ala$^7$,Lys$^{24}$]salmon calcitonin, 53 mg of 2,4,5-trichlorophenyl formate and 0.081 ml N-ethyl-diisopropylamine in 8 ml of DMF are stirred at room temperature for 15 hours. 200 ml of ether are added, the precipitate filtered, washed with ether and dried. The product is purified by reversed-phase chromatography on C-18 silica using a gradient of acetonitrile in 2% phosphoric acid. Fractions containing the pure product are collected and filtered over a column of a basic ion-exchange resin in the acetate form and washed with water. The filtrate is lyophilised and the title compound is obtained as a polyacetate, polyhydrate.

$[\alpha]_D^{20}=-28.3°$ (c=0.24 in 95% AcOH), F=0.93

FAB-mass spectroscopy: MH$^+$=3138.1.

EXAMPLE 13

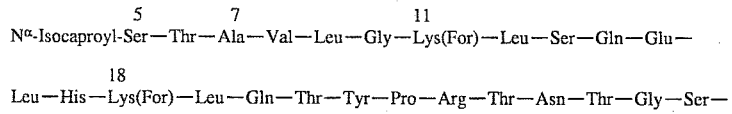

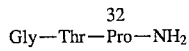
Gly—Thr—Pro—NH₂

This compound is obtained in analogous manner to Example 12 starting from N$^\alpha$-isocaproyl-des(1-4)-[Ala⁷] salmon calcitonin.

$[\alpha]_D^{20}$=−26.5° (c=0.2 in 95% AcOH), F=0.99

FAB-MS: =3138.7 (MH⁺).

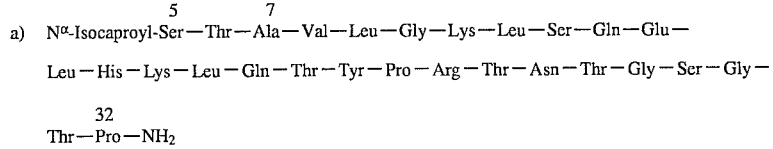

This compound is obtained in analogous manner to Example 7a.

$[\alpha]_D^{20}$=−32.2° (c=0.3 in 95% AcOH), F=0.87.

EXAMPLE 14

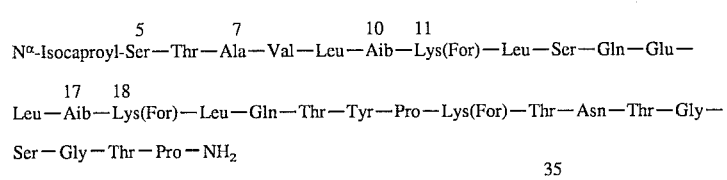

This compound is obtained in analogous manner to Example 12 starting form N$^\alpha$-isocaproyl-des(1-4)-[Ala⁷, Aib¹⁰,¹⁷,Lys²⁴]salmon calcitonin.

$[\alpha]_D^{20}$=−36.5° (c=0.26 in 95% AcOH), F=0.98

(The preparation of the starting material is described in Example 16).

EXAMPLE 15

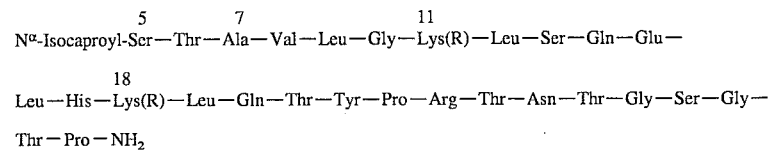

R=(2S)-2,3-dihydroxypropyl- 100 mg of N$^\alpha$-Isocaproyl-des(1-4)-[Ala⁷]salmon calcitonin, 16.4 mg of NaCNBH₃ and 11.7 mg of D-(+)-glycerinaldehyde are dissolved in 2 ml of Methanol and 1 ml of water, the reaction mixture is adjusted to pH 6 by the addition of 0.1N HCl and stirred at room temperature for 30 hours. The reaction mixture is acidified to pH 2 with HCl, stirred for 2 hours and solvents removed under reduced pressure. The residue is chromatographied on a C-18 silica column using a gradient of acetonitrile in 10 mM NaH₂PO₄. Fractions containing the pure product are collected, filtered over a column of a basic ion-exchange resin in the acetate form and washed with water. The filtrate is lyophised and the title compound obtained as a polyacetate, polyhydrate.

$[\alpha]_D^{20}$=−23.9° (c=0.1 in 95% AcOH), F=0.79

FAB-MS: =3230.6 (MH⁺).

The following examples 16, 17, 18 and 20 are prepared in an analogous manner to Example 15:

EXAMPLE 16

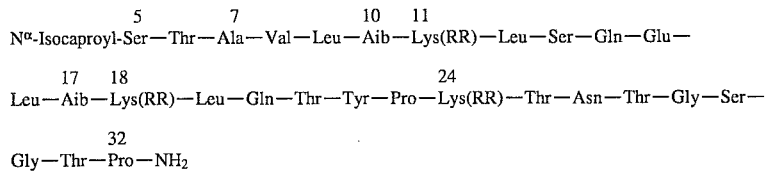

R=CH$_2$CH$_2$-OH

Starting from N$^\alpha$-isocaproyl-des(1-4)-[Ala$^7$,Aib$^{10,17}$Lys$^{24}$]salmon calcitonin and using a 20-fold molar excess of glycolaldehyde and NaCNBH$_3$ at pH 5 and 45° C. for 15 hours the title compound is obtained after purification.

$[\alpha]_D^{20}$=−72.0° (c=0.3 in 95% AcOH), F=0.77.

a) The starting material, N$^\alpha$-isocaproyl-des(1-4)-Ala$^7$, Aib$^{10,17}$, Lys$^{24}$]salmon calcitonin, is obtained in an analogous manner to Example 7a by using for incorporation Boc-Lys(2-chloro-benzyloxy-carbonyl)-OH in position 24 and Boc-Aib-OH in positions 17 and 10 of the stepwise synthesis.

EXAMPLE 17

N$^\alpha$-Isocaproyl-Ser—Thr—Ala—Val—Leu—Aib—Lys(For)—Leu—Ser—Gln—Glu— (5, 7, 10, 11)

Leu—Aib—Lys(For)—Leu—Gln—Thr—Tyr—Pro—Lys(R,R)—Thr—Asn—Thr—Gly— (17, 18)

Ser—Gly—Thr—Pro—NH$_2$

R=CH$_2$OH

The title compound is obtained starting from N$^\alpha$-isocaproyl-des(1-4)-[Ala$^7$,Aib$^{10,17}$,Lys(For)$^{11,18}$,Lys$^{24}$]salmon calcitonin and using the conditions of Example 16.

$[\alpha]_D^{20}$=−63.9° (c=0.3 in 95% AcOH), F=0.76.

EXAMPLE 18

N$^\alpha$-Isocaproyl-Ser—Thr—Ala—Val—Leu—Aib—Lys(For)—Leu—Ser—Gln—Glu— (5, 7, 10, 11)

Leu—Aib—Lys(For)—Leu—Gln—Thr—Tyr—Pro—Lys(R)—Thr—Asn—Thr—Gly— (17, 18)

Ser—Gly—Thr—Pro—NH$_2$

R=2,3-0,0'-isopropylidene-(2S)-2,3-dihydroxy-propyl

The title compound is obtained starting from N$^\alpha$-isocaproyl-des(1-4)-]Ala$^7$,Aib$^{10,17}$,Lys(For)$^{11,18}$,Lys$^{24}$]salmon calcitonin and the 2,3-0,0'-isopropylidene derivative of D(+)-glyceraldehyde and separating the mono- from the disubstituted compound by reversed-phase chromatography using a gradient of acetonitrile in 10 mM NaH$_2$PO$_4$.

$[\alpha]_D^{20}$=−59.0° (c=0.14 in 95% AcOH), F=0.94

FAB-MS: 3203 (MH$^+$).

EXAMPLE 19

N$^\alpha$-Isocaproyl-Ser—Thr—Ala—Val—Leu—Aib—Lys(For)—Leu—Ser—Gln—Glu— (5, 7, 10, 11)

Leu—Aib—Lys(For)—Leu—Gln—Thr—Tyr—Pro—Lys(R)—Thr—Asn—Thr—Gly— (17, 18)

Ser—Gly—Thr—Pro—NH2

R=(2S)-2,3-dihydroxypropyl-

The title compound is obtained by treating the compound of Example 18 with a mixture of 5% water in TFA at room temperature for 10 minutes, precipitating the product by the addition of ether and purification as in Example 15.

$[\alpha]_D^{20}$=−65.8° (c=0.11 in 95% AcOH), F=0.97

FAB-MS: 3162 (MH$^+$).

EXAMPLE 20

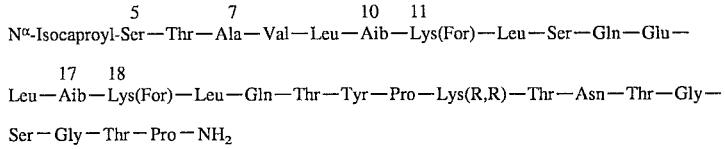

R=2,3-0,0'-isopropylidene-(2S)-2,3-dihydroxy-propyl

The title compound is obtained as in Example 18 by isolating the di-substituted compound from the reaction mixture.

$[\alpha]_D^{20} = -57.6°$ (c=0.1 in 95% AcOH), F=0.94

FAB-MS: 3318 (MH$^+$).

EXAMPLE 21

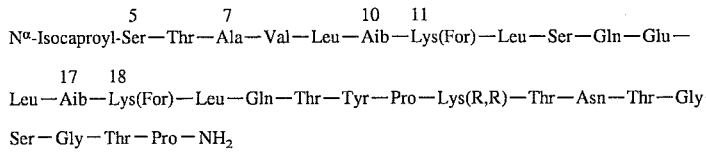

R=(2S)-2,3-dihydroxypropyl-

This compound is obtained from Example 20 by the procedure of Example 19.

$[\alpha]_D^{20} = -49.5°$ (c=0.06 in 95% AcOH), F=0.89

FAB-MS: 3234.2 (MH$^+$).

EXAMPLE 22

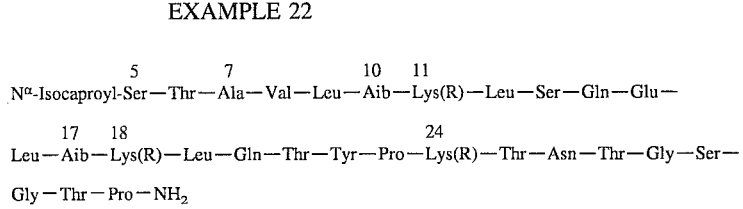

R=N$^\epsilon$-isopropyl 150 mg of N$^\alpha$-isocaproyl-des(1-4)-[Ala$^7$,Aib$^{10,17}$,Lys$^{24}$] salmon calcitonin of Example 16 and 187 mg NaCNBH$_3$ are dissolved in a mixture of 3 ml methanol, 7 ml of phosphate buffer at pH 5.0 and 3 ml of acetone and stirred at 45° C. for 16 hours. The reaction mixture is diluted with 50 ml of water, filtered over a column of a polystyrene absorption resin, washed with water and eluted with ethanol 60% in water. Fractions containing the product are collected and lyophilised. The residue is chromatographied on a C-18 silica column using a gradient of acetonitrile in H$_3$PO$_4$ 2%. Fractions containing the pure product are collected, filtered over a column of a basic ion exchange resin in the acetate form and washed with water. The filtrate is lyophilised and the title compound obtained as a polyacetate, polyhydrate.

$[\alpha]_D^{20} = -76.7°$ (c=0.23 in 95% AcOH), F=0.71

FAB-MS: 3158 (MH$^+$).

(The preparation of the starting material is described in Example 16).

EXAMPLE 23

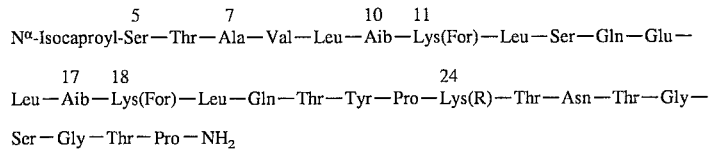

R=N$^\epsilon$-isopropyl

This compound is prepared in analogous manner to Example 22 starting from N$^\alpha$-isocaproyl-des(1-4)-[Ala$^7$,Aib$^{10,17}$,Lys(For)$^{11,18}$,Lys$^{24}$]salmon calcitonin.

$[\alpha]_D^{20}=-71.2°$ (c=0.11 in 95% AcOH), F=1.00

FAB-MS: 3128.6 (MH⁺).

(The preparation of the starting material is described in Example 24).

EXAMPLE 24

$$\overset{5}{N^\alpha\text{-Isocaproyl-Ser}}-\overset{7}{\text{Thr}}-\text{Ala}-\text{Val}-\text{Leu}-\overset{10}{\text{Aib}}-\overset{11}{\text{Lys(For)}}-\text{Leu}-\text{Ser}-\text{Gln}-\text{Glu}-$$

$$\overset{17}{\text{Leu}}-\overset{18}{\text{Aib}}-\text{Lys(For)}-\text{Leu}-\text{Gln}-\text{Thr}-\text{Tyr}-\text{Pro}-\overset{24}{\text{Lys}}-\text{Thr}-\text{Asn}-\text{Thr}-\text{Gly}-\text{Ser}-$$

$$\text{Gly}-\text{Thr}-\text{Pro}-\text{NH}_2$$

This is obtained in an analogous manner to Example 7a by using for incorporation Boc-Lys(For)-OH in position 11 and 18, Boc-Aib-OH in position 10 and 17 and Boc-Lys(2-chlorobenzyloxy-carbonyl)-OH in position 24 of the stepwise synthesis. Purification as described for Example 18 gives the title compound.

$[\alpha]_D^{20}=-76.5°$ (c=0.12 in 95% AcOH), F=0.90

FAB-MS: 3088 (MH⁺).

EXAMPLE 25

N(alpha)-Isocaproyl-Ser5-Thr-Ala7-Val-Leu-Aib10-Lys(R)11-Leu-Ser-Gln-Glu-Leu-Aib 17-Lys(R)18-Leu-Gln-Thr-Tyr-Pro-Lys(R)24-Thr-Asn-Thr-Gly-Ser-Gly-Thr-Pro-NH2
R=N(epsylon)-(2S)-2,3-dihydroxypropyl This peptide is assembled in a stepwise manner on a polystyrene-based resin support. The Fmoc-group is used for protection of the alpha amino-groups. Side-chain functional groups are protected as Ser(tBu), Thr(tBu), Tyr(tBu), and Glu(OtBu). N(epsylon)-(2S)-2,3-dihydroxypropyl-lysine is incorporated using N(alpha)-Fmoc-N(epsylon)-Boc-N(epsylon)-O,O'-isopropylidene-(2S)2,3-dihydroxypropyl-lysine the preparation of which is described in Example 9. 4-(2',4'-Dimethoxyphenyl-Fmoc-aminomethyl)-phenoxy-co(polystyrene-divinylbenzene), 0.4 mmol/g, which may be prepared as described in Tetrah.letters, Vol. 28, 3787–3790 (1987) is subjected to the following cycle, steps (1) to (5), of treatments:

(1) washing with DMF
(2) piperidine (20%) in DMF
(3) DMF
(4) mixture of HOBt, diisopropylcarbodiimide, and Fmoc-amino acid 0.8 mmol per gram starting resin each)
(5) DMF Volumes of washes and reagents are from 5 to 20 ml per gram of starting resin.

Each step is repeated as many times as necessary for either complete reaction of the resin (steps 2, 4) or complete displacement of the previous reagent(s) from the resin (steps 3, 5). Samples of the resin are removed after each cycle and checked for completeness of the coupling reaction by a colorimetric test for residual amino groups using ninhydrin.

The cycle of treatments, (1) to (5), is repeated for each amino acid residue such as to provide the sequence of the title compound.

In the last cycle, in step (4), isocaproic acid, diisopropylcarbodiimide and HOBt (all at 3.5 mmol per g of starting resin) in DMF are added to the resin. After 15 hours, the resin is washed with DMF and DCM and dried.

The peptide resin (1 g) is suspended in a mixture of 5% water in TFA. After 1 hour at room temperature, the resin particles are filtered off and washed with TFA 95%. The product is precipitated from the combined filtrates by the addition of ether, filtered, washed with ether and dried. The product is chromatographed on a C-18 silica column using a gradient of acetonitrile in 2% H3PO4. Fractions containing the pure compound are collected, filtered through a basic ion-exchange resin in the acetate form, lyophilised and the title compound obtained as the polyacetate, polyhydrate.

$[\alpha]_D^{20}=-73°$ (c=0.36 in 95% AcOH)

F=0.91

FAB-MS: 3253.1 (MH+)

Abbreviations

Lys(For)=N-formyl-lysine
Aib=-amino-isobutyric acid
HOBt=1-hydroxybenzotriazole

The compounds of the invention in free form or in the form of pharmaceutically acceptable salts and complexes exhibit valuable pharmacological properties as indicated in animal tests and are, therefore, indicated for therapy.

The calcitonin compounds of the invention, particularly the compounds of formula X, lower the calcium plasma level. They are also functional antagonists of the parathormone and effect a positive calcium balance in bones.

The hypocalcemic effect of the compounds may be observed in conventional manner, for example according to the method of M. Azria et al. reported in Calcitonin 1984 symposium 24th October, Milan published in 1986 as Short Communications in the Current Clinical Practice Series No. 42, Excerpta Medica 1986, p. 104. In this method a calcium [2+] ion selective electrode is used to measure continuously the calcium ion content in blood of rabbits. The compounds are administered i.v. at a dose of from 0.02 to about 20 microgram/kg body weight. The measurements are effected over 5 to 10 hours and the area under the curve measured.

The compounds can also be tested in other tests, e.g. the hypocalcemic test of M. Kumar et al., J. Endocrinology, (1965), 33, p. 469 in rats at the same doses. A hypocalcemic activity of from 50 to 7000 IU/mg is observed for the calcination compounds of the invention.

The calcitonin compounds of the invention are accordingly indicated for use in the treatment of conditions in which it is desirable to reduce or to normalize the plasma calcium level or to influence bone metabolism, e.g. hypercalcaemia as a result of endogenic thyrocalcitonin deficiency through loss of thyroid tissue or hyperfunction of the parathyroid. They are also indicated for use in the treatment of all bone conditions which are associated with increased degradation or in which calcium fixation in the bones is desirable, e.g. osteoporosis of various causes (e.g. post-climacteric, post-traumatic, caused by cortico-steroid therapy or inactivity, for malignant illnesses etc.), fractures, osteo-malacia, rickets and renally-induced osterdystrophy, pain e.g. bone pain associated with osteoporosis, neurodystrophic diseases, Paget's disease, as well as in particular for combined therapy with calcium or phosphates or fluoride or one or several steroid hormones or pTH and its bioactive fragments or analogues, or combinations thereof.

For these indications, the appropriate dosage will, of course, vary depending upon, for example, the compound of the invention employed, the host, the mode of administration and the nature and severity of the condition being treated. However, in general, satisfactory results in animals are indicated to be obtained at daily dosages from about 0.1 µg/kg to 20 mg/kg animal body weight. In larger mammals, for example humans, an indicated daily dosage is in the range from about 2 µg to about 20 mg of a calcitonin peptide of the invention.

The calcitonin compounds according to the invention also inhibit pancreas secretion. This inhibition may be shown in animals, e.g. using the method described in Scand. J. Gastroint. 6, (1975) by S. J. Konturek et al., at the same dosages indicated above.

The compounds according to the invention are therefore further useful for the treatment of acute pancreatitis and gastro-intestinal disorders such as ulcers.

For these indications, the appropriate dosage will, of course, vary depending upon, for example, the compound of the invention employed, the host, the mode of administration and the nature and severity of the condition being treated. However, in general, satisfactory results in animals are indicated to be obtained at daily dosage from about 0.1 µg/kg to 20 mg/kg animal body weight. In larger mammals, for example humans, an indicated daily dosage is in the range from about 2 µg to about 20 mg of a calcitonin peptide of the invention.

The compounds of Example 7 and 11 are preferred. It has, for example, been determined that these compounds have about 100–130 per cent of the activity of salmon calcitonin in the hypocalcemic test of M. Azria et al. It is therefore indicated that these compounds may be administered at similar or lower dosages than conventionally employed for salmon calcitonin.

The calcitonin peptides of the invention may be administered by any conventional route, in particular nasally, enterally, e.g. orally e.g. in the form of tablets or capsules, or parenterally, e.g. in the form of injectable solutions or suspensions, or a suppository form. They may also be administered in sustained release form.

The calcitonin peptides may be administered in free form or in pharmaceutically acceptable salt form or complexes. Such salts and complexes may be prepared in conventional manner and exhibit the same order of activity as the free compounds. The present invention also provides a pharmaceutical composition comprising a calcitonin peptide as defined above in free form or in pharmaceutically acceptable salt form or complex form in association with a pharmaceutically acceptable diluet or carrier. Such compositions may be formulated in conventional manner. Unit dosage forms contain, for example, from about 0.5 µg to about 10 mg of a calcitonin peptide of the invention.

The LHRH antagonists of the invention, in particular the compounds of formula XI inhibit luteinizing hormone secretion, e.g. as indicated by an inhibition of ovulation in animals. This test is effected according to M. Marko and E. Flückiger, Experientia 30, 1174–1776 (1974).

Adult female rats of the Ivanovas Wistar strain (Sprague Dawley, Iva: SDIV, 200–250 g) are kept under standard conditions: 14 h light (from 0.400 to 18.00 hours); 24° C.; 55–60% rel. humidity; food and water ad libitum. Animals with regular 4-day cycles are injected on proestrus day at 13.00 h with the compound to be tested, subcutaneously or by the oral route. The next day at 9:00 a.m. the rats are sacrified and ova counted on both Fallopian tubes with the aid of a dissecting microscope. Only when no eggs are found is ovulation considered to be inhibited. The mean number of eggs per ovulating rat in each treatment groups is also determined.

The LHRH antagonists of the invention are active in this test when administered at a dosage in a range from about 0.0005 to about 10 mg/kg s.c.

The inhibiting effect on luteinizing hormone secretion of the LHRH antagonists of the invention can also be tested in vitro:

Rat pituitary cell cultures are prepared according to the method of Vale (W. Vale and G. Grant; Methods in Enzymology 37, 82–93 (1975) as has been described previously (M. Marko and D. Römer: Life Sciences, 33, 233–240 (1983). Primary cultures are maintained for 4 days in an incubator at 37° C. Thereafter the cells are washed and incubated for 3 hours in a medium containing LHRH together with the test compound at different concentrations. At the end of the incubation, the supernatant is removed and assayed for LH by specific radioimmunoassay. In general the LHRH antagonist peptides show antagonistic effects against LHRH in a concentration below $10^{-7}$M.

The LHRH antagonists of the invention are accordingly indicated for use in the treatment of conditions making a suppression of gonadotropic secretion medically desirable such as pubertas praecox, mammary cancer, prostatic hypertrophy and prostatic cancer, endometriosis, and gonadotropin secreting pituitary tumors, and for suppressing ovulation in female and spermtogenesis in male.

For these indications, the appropriate dosage will, of course, vary depending upon, for example, the compound of the invention employed, the host, the mode of administration and the nature and severity of the condition being treated. However, in general, satisfactory results in animals are indicated to be obtained at daily dosages from about 0.1 µg/kg to 20 mg/kg animal body weight. In larger mammals, for example humans, an indicated daily dosage is in the range from about 10 µg to about 100 mg of the invention.

In the above mentioned test for inhibition of ovulation in female rats, the compound of Example 4 has e.g. an $ED_{50}$ of 3 µg/kg after s.c. and 300 µg/kg after oral application compared to 80 µg/kg s.c. of [N-Ac-DPhe(Cl)$^{1,2}$, DTrp$^3$, DAla$^{10}$]-LHRH (J. Erchegyi et al., BBRC 100, 95) in the same test. It is therefore indicated that the Example 4 compound may be administered e.g. at daily dosages of from 1 to 100 mg to larger mammals, for example humans.

The LHRH antagonists of the invention may be administered by any conventional route, in particular nasally, enterally, e.g. orally e.g. in the form of tablets or capsules, or parenterally, e.g. in the form of injectable solutions or suspensions, or a suppository form. They may also be administered in sustained release form.

The LHRH peptide of Example 4 is the preferred compound.

The LHRH antagonists of the invention may be administered in free form or in pharmaceutically acceptable salt form or complexes. Such salts and complexes may be prepared in conventional manner and exhibit the same order of activity as the free compounds. The present invention also provides a pharmaceutical composition comprising a LHRH antagonist in free form or in pharmaceutically acceptable salt form or complex form in association with a pharmaceutically acceptable diluent or carrier. Such compositions may be formulated in conventional manner. Unit dosage forms contain, for example, from about 5 μg to about 10 mg of a LHRH antagonist of the invention.

In accordance with the foregoing the present invention further provides:

a) a compound of the invention, e.g. a calcitonin or LHRH antagonist peptide as defined, for example a compound of formula X or XI, or a pharmaceutically acceptable salt or complex thereof for use as a pharmaceutical;

b) a method of treating a disorder such as indicated above, in a subject in need of such treatment, which method comprises administering to said subject an effective amount of a compound according to the invention, e.g. a calcitonin or LHRH peptide as defined above, for example a compound of formula X or XI, or a pharmaceutically acceptable salt or complex thereof, respectively.

One group of compounds in accordance with the invention is a group of calcitonins bearing in the 24 position an α-amino-acid which is further substituted in the alpha position by an ω-amino-$C_{1-6}$alkyl residue and containing at least one formyl group preferably in 24 position, in free form or in salt or complex form.

Another group of compounds in accordance with the invention is a group of calcitonins bearing in the 24 position an α-amino-acid which is further substituted in the alpha position by an ω-amino-$C_{1-6}$alkyl residue and containing at least one sugar residue preferably in 24 position, in free form or in salt or complex form.

A further group of compounds in accordance with the invention is a group of calcitonins bearing in the 24 position an α-amino-acid which is further substituted in the alpha position by an ω-amino-$C_{1-6}$alkyl residue and containing at least one sugar residue and at least one formyl group, in free form or in salt or complex form.

A further group of compounds in accordance with the invention is a group comprising LHRH antagonists bearing in position 8 an α-amino-acid which has a ω-amino-$C_{1-6}$alkyl side chain group substituted in ω position by an Amadori sugar residue, in free form or in salt or complex form.

In a series of specific embodiments, the present invention also provides a calcitonin peptide comprising attached to an amino group thereof at least a) one sugar residue, and/or b) one residue of formula ($b_1$) or ($b_2$) as defined above with the proviso that when the calcitonin peptide comprises at least one sugar residue a), this sugar residue is attached by a coupling other than a direct N-glycosidic bond to an ω-amino group of an ω-amino substituted side chain in the 24 position.

In a further embodiment, the present invention also provides a calcitonin peptide comprising d) at least one formyl attached to an amino group other than a N-terminal amino group, and/or e) at least one $C_{3-5}$alkyl attached to an amino group other than a N-terminal amino group, or a calcitonin peptide bearing as substituents any combination of a), b), d) and e) as defined above.

In a further embodiment, the present invention also provides a LHRH antagonist peptide comprising attached to an amino group thereof at least a) one sugar residue, and/or b) one residue of formula ($b_1$) or ($b_2$) as defined above with the proviso that when the LHRH antagonist comprises at least one sugar residue a), this sugar residue is an Amadori sugar residue attached by a coupling other than a direct N-glycosidic bond to an ω-amino group of an ω-amino substituted side chain in the 8 position.

What is claimed is:

1. A calcitonin peptide selected from the group consisting of

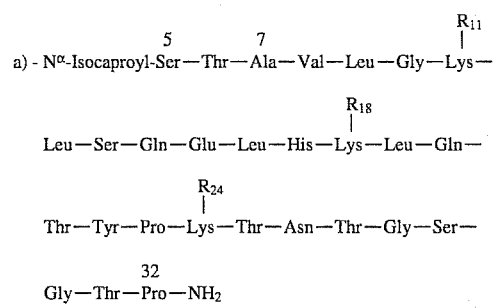

where R in the 11, 18, and 24 position is $N^\epsilon$-1-deoxyfructosyl;

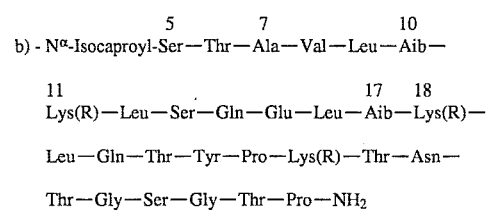

where R is $N^\epsilon$-1-deoxyfructosyl;

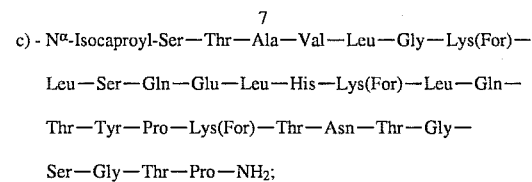

-continued d) - N$^\alpha$-Isocaproyl-Ser—Thr—Ala—Val—Leu—Aib—Lys(For)—
     $\overset{5}{}$ $\overset{7}{}$ $\overset{10}{}$ $\overset{11}{}$
Leu—Ser—Gln—Glu—Leu—Aib—Lys(For)—Leu—Gln—
     $\overset{17}{}$ $\overset{18}{}$
Thr—Tyr—Pro—Lys(For)—Thr—Asn—Thr—Gly—Ser—
Gly—Thr—Pro—NH$_2$;

e) - N$^\alpha$-Isocaproyl-Ser—Thr—Ala—Val—Leu—Aib—Lys(RR)—
     $\overset{5}{}$ $\overset{7}{}$ $\overset{10}{}$ $\overset{11}{}$
Leu—Ser—Gln—Glu—Leu—Aib—Lys(RR)—Leu—Gln—
     $\overset{17}{}$ $\overset{18}{}$
Thr—Tyr—Pro—Lys(RR)—Thr—Asn—Thr—Gly—
     $\overset{24}{}$
Ser—Gly—Thr—Pro—NH$_2$
     $\overset{32}{}$ where R is -CH$_2$CH$_2$-OH;

f) - N$^\alpha$-Isocaproyl-Ser—Thr—Ala—Val—Leu—Aib—Lys(For)—
     $\overset{5}{}$ $\overset{7}{}$ $\overset{10}{}$ $\overset{11}{}$
Leu—Ser—Gln—Glu—Leu—Aib—Lys(For)—Leu—Gln—
     $\overset{17}{}$ $\overset{18}{}$
Thr—Tyr—Pro—Lys(R,R)—Thr—Asn—Thr—Gly—Ser—
Gly—Thr—Pro—NH$_2$ where R is -CH$_2$CH$_2$OH;

g) - N$^\alpha$-Isocaproyl-Ser—Thr—Ala—Val—Leu—Aib—Lys(For)—
     $\overset{5}{}$ $\overset{7}{}$ $\overset{10}{}$ $\overset{11}{}$
Leu—Ser—Gln—Glu—Leu—Aib—Lys(For)—Leu—Gln—
     $\overset{17}{}$ $\overset{18}{}$
Thr—Tyr—Pro—Lys(R)—Thr—Asn—Thr—Gly—Ser—
Gly—Thr—Pro—NH$_2$ where R is 2,3-O,O'-isopropylidene-(2S)-dihydroxypropyl-;

h) - N$^\alpha$-Isocaproyl-Ser—Thr—Ala—Val—Leu—Aib—Lys(For)—
     $\overset{5}{}$ $\overset{7}{}$ $\overset{10}{}$ $\overset{11}{}$
Leu—Ser—Gln—Glu—Leu—Aib—Lys(For)—Leu—Gln—
     $\overset{17}{}$ $\overset{18}{}$
Thr—Tyr—Pro—Lys(R)—Thr—Asn—Thr—Gly—Ser—
Gly—Thr—Pro—NH2 where R is (2S)-2,3-dihydroxypropyl-;

i) - N$^\alpha$-Isocaproyl-Ser—Thr—Ala—Val—Leu—Aib—Lys(For)—
     $\overset{5}{}$ $\overset{7}{}$ $\overset{10}{}$ $\overset{11}{}$
Leu—Ser—Gln—Glu—Leu—Aib—Lys(For)—Leu—Gln—
     $\overset{17}{}$ $\overset{18}{}$
Thr—Tyr—Pro—Lys(R,R)—Thr—Asn—Thr—Gly—Ser—
Gly—Thr—Pro—NH$_2$ where R is 2,3-O,O'-isopropylidene-(2S)-2,3-dihydroxypropyl-;

j) - N$^\alpha$-Isocaproyl-Ser—Thr—Ala—Val—Leu—Aib—Lys(For)—
     $\overset{5}{}$ $\overset{7}{}$ $\overset{10}{}$ $\overset{11}{}$
Leu—Ser—Gln—Glu—Leu—Aib—Lys(For)—Leu—Gln—
     $\overset{17}{}$ $\overset{18}{}$
Thr—Tyr—Pro—Lys(R,R)—Thr—Asn—Thr—Gly—Ser—
Gly—Thr—Pro—NH$_2$ where R is (2S)-2,3-dihydroxypropyl-;

k) - N$^\alpha$-Isocaproyl-Ser—Thr—Ala—Val—Leu—Aib—Lys(R)—
     $\overset{5}{}$ $\overset{7}{}$ $\overset{10}{}$ $\overset{11}{}$
Leu—Ser—Gln—Glu—Leu—Aib—Lys(R)—Leu—Gln—
     $\overset{17}{}$ $\overset{18}{}$
Thr—Tyr—Pro—Lys(R)—Thr—Asn—Thr—Gly—Ser—
     $\overset{24}{}$
Gly—Thr—Pro—NH$_2$ where R is N$^\epsilon$-isopropyl-;

l) - N$^\alpha$-Isocaproyl-Ser—Thr—Ala—Val—Leu—Aib—Lys(For)—
     $\overset{5}{}$ $\overset{7}{}$ $\overset{10}{}$ $\overset{11}{}$
Leu—Ser—Gln—Glu—Leu—Aib—Lys(For)—Leu—Gln—
     $\overset{17}{}$ $\overset{18}{}$
Thr—Tyr—Pro—Lys(R)—Thr—Asn—Thr—Gly—Ser—
     $\overset{24}{}$
Gly—Thr—Pro—NH$_2$ where R is N$^\epsilon$-isopropyl-;

m) - N$^\alpha$-Isocaproyl-Ser—Thr—Ala—Val—Leu—Aib—
     $\overset{5}{}$ $\overset{7}{}$ $\overset{10}{}$
Lys(For)—Leu—Ser—Gln—Glu—Leu—Aib—Lys(For)—
     $\overset{11}{}$ $\overset{17}{}$ $\overset{18}{}$
Leu—Gln—Thr—Tyr—Pro—Lys—Thr—Asn—Thr—
     $\overset{24}{}$
Gly—Ser—Gly—Thr—Pro—NH$_2$;

n) - N$^\alpha$-Isocaproyl-Ser—Thr—Al —Val—Leu—Aib—Lys(R)—
Leu—Ser—Gln—Glu—Leu—Aib—Lys(R)—Leu—Gln—
Thr—Tyr—Pro—Lys—Thr—Asn—Thr—Gly—Ser—
Gly—Thr—Pro—NH$_2$ where R is N$^\epsilon$-2(S)-2,3-dihydroxypropyl-; and o) - N$^\alpha$-Isocaproyl-Ser—Thr—Ala—Val—Leu—Aib—Lys(For)—
     $\overset{5}{}$ $\overset{7}{}$ $\overset{10}{}$ $\overset{11}{}$
Leu—Ser—Gln—Glu—Leu—Aib—Lys(For)—Leu—Gln—
     $\overset{17}{}$ $\overset{18}{}$
Thr—Tyr—Pro—Lys(R)—Thr—Asn—Thr—Gly—Ser—
Gly—Thr—Pro—NH$_2$ where R is N$^\epsilon$-1-deoxyfructosyl
in free form or in salt or complex form.

2. A method of treating a condition requiring a reduction or normalization of the plasma calcium level or an influence on bone metabolism, or bone conditions associated with increased degradation or in which calcium fixation in bones is desirable, or of acute pancreatitis and gastrointestinal disorders, in a subject in need of such treatment, which comprises administering to said subject an amount effective for said treatment of a calcitonin peptide of claim 1 in free form or in pharmaceutically acceptable salt or complex form.

3. A pharmaceutical composition comprising a therapeutically effective amount of a calcitonin peptide of claim 1 in free form or in pharmaceutically acceptable salt form or complex form and a pharmaceutically acceptable carrier therefor.

4. The calcitonin peptide according to claim 1 which is $$N^{\alpha}\text{-Isocaproyl}-\underset{5}{Ser}-Thr-\underset{7}{Ala}-Val-Leu-\underset{10}{Aib}-$$
$$\underset{11}{Lys(For)}-Leu-Ser-Gln-Glu-Leu-\underset{17}{Aib}-\underset{18}{Lys(For)}-$$
$$Leu-Gln-Thr-Tyr-Pro-Lys(R)-Thr-Asn-Thr-$$
$$Gly-Ser-Gly-Thr-Pro-NH_2$$

where R is $N^{\epsilon}$-1-deoxyfructosyl,
in free form or in pharmaceutically acceptable salt or complex form.

* * * * *